United States Patent [19]

Sanderson et al.

[11] Patent Number: 4,691,034
[45] Date of Patent: Sep. 1, 1987

[54] PURIFICATION OF PROPYLENE OXIDE BY TREATMENT WITH CALCIUM HYDROXIDE IN GLYCEROL OR SUGAR WATER

[75] Inventors: John R. Sanderson; William A. Smith; Edward T. Marquis, all of Austin; Kenneth P. Keating, Georgetown, all of Tex.

[73] Assignee: Texaco, Inc., White Plains, N.Y.

[21] Appl. No.: 851,842

[22] Filed: Apr. 14, 1986

[51] Int. Cl.$^4$ ............................................ C07D 301/32
[52] U.S. Cl. ................................................. 549/542
[58] Field of Search ........................................ 549/542

[56] References Cited

U.S. PATENT DOCUMENTS

| | | | |
|---|---|---|---|
| 2,550,847 | 5/1951 | Mitchell et al. | 549/542 |
| 2,622,060 | 12/1952 | Robeson et al. | 549/542 |
| 3,350,417 | 10/1967 | Binning et al. | 549/532 |
| 3,477,919 | 11/1969 | Lichtenwalter et al. | 549/542 |
| 3,838,020 | 9/1974 | Kageyama et al. | 549/541 |
| 4,243,492 | 1/1981 | Yamamura et al. | 549/542 |

FOREIGN PATENT DOCUMENTS

| | | | |
|---|---|---|---|
| 2108922 | 8/1972 | Fed. Rep. of Germany | 549/542 |
| 4718811 | 9/1972 | Japan | 549/542 |

*Primary Examiner*—Norma S. Milestone
*Attorney, Agent, or Firm*—Jack H. Park; Kenneth R. Priem; Richard A. Morgan

[57] ABSTRACT

Methyl formate is removed from propylene oxide by treatment with aqueous calcium hydroxide slurry. Calcium hydroxide solubility is increased by adding a solubilizer selected from the group consisting of sucrose, fructose, maltose, glycerol and mixtures thereof. Methyl formate hydrolysis rate is improved by propylene oxide/water ratio control. Addition of an aldehyde scavenger improves propylene oxide purity.

18 Claims, 1 Drawing Figure

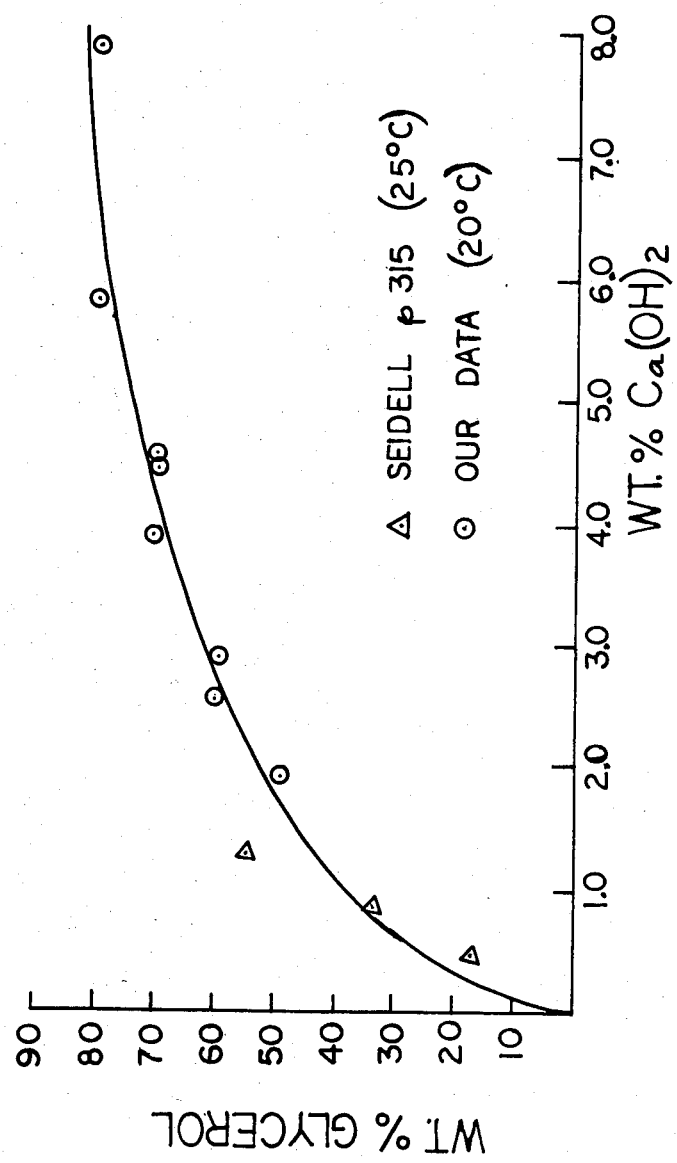

PURIFICATION OF PROPYLENE OXIDE BY TREATMENT WITH CALCIUM HYDROXIDE IN GLYCEROL OR SUGAR WATER

CROSS-REFERENCE TO RELATED APPLICATION

This application is related to U.S. patent application Ser. No. 851,846 filed on even date and incorporated herein by reference which relates to propylene oxide purification with weak bases and inert salts.

BACKGROUND OF THE INVENTION

It is known to prepare propylene oxide by the oxidation of aliphatic hydrocarbons such as propane or butane, or the oxidation of an olefin such as propylene.

In the Oxirane process, propylene oxide is prepared by the catalytic epoxidation of propylene with a hydroperoxide. In the process, isobutane is oxidized in the liquid phase without catalyst at 120° to 140° C. and 450 to 500 psig. The resultant liquid is a mixture of reactant hydrocarbons, t-butyl hydroperoxide, t-butyl alcohol, acetone and lesser quantities of other by-products such as ketones, aldehydes, and acids.

Many of the by-products are carried over with the t-butyl hydroperoxide into the second reaction. In the second reaction, propylene is catalytically epoxidized with t-butyl hydroperoxide in liquid phase at high pressure to form propylene oxide. The preferred catalyst is a molybdenum naphthenate organic solution which has a 90 mol percent selectivity on propylene.

The reactions result in complex mixtures containing a number of oxidation products in addition to the propylene oxide. By-products include t-butyl alcohol, ethers, acids, glycols and esters such as methyl formate. Methyl formate has a boiling point near that of propylene oxide, making separation of the two by distillation impractical. In order to obtain propylene oxide suitable for applications, such as the manufacture of polyether polyols used in the preparation of polyurethanes, it is necessary to remove the methyl formate from the propylene oxide.

U.S. Pat. No. 3,477,919 teaches a method for purifying propylene oxide. Propylene oxide prepared by the oxidation of propylene is contaminated with impurities which boil near propylene oxide. The methyl formate impurity is removed from the contaminated propylene oxide by reaction with an aqueous slurry of calcium hydroxide.

U.S. Pat. No. 2,622,060 teaches a process for separating propylene oxide from a crude reaction mixture by treatment with an aqueous alkali metal hydroxide solution.

U.S. Pat. No. 2,550,847 teaches a process for the purification of propylene oxide in a crude reaction mixture containing methyl formate by subjecting the mixture to strong agitation with an aqueous solution of an alkaline saponifying agent.

U.S. Pat. No. 3,350,417 teaches a process for purifying propylene oxide comprising parallel and serial stages of distillation and a caustic treatment to simultaneously aldolize acetaldehyde and saponify methyl formate.

U.S. Pat. No. 3,838,020 teaches a process for purifying propylene oxide by extractive distillation with a dual solvent system.

All of these procedures are inherently inefficient in their removal of methyl formate and aldehydes. All of the procedures teach methods which suffer from the disadvantage of hydrolysis of propylene oxide to propylene glycol resulting in a depletion of the desired propylene oxide product.

The instant invention is a practical and complete method of removing methyl formate and aldehydes accomplished without significant loss of propylene oxide.

SUMMARY OF THE INVENTION

An improved method has been discovered for removing methyl formate from propylene oxide prepared by the oxidation of alkanes or olefins, without appreciable hydrolysis of propylene oxide to propylene glycol. By the method the contaminated propylene oxide is contacted with an aqueous calcium hydroxide and a solubilizing amount of sucrose, fructose, maltose, glycerol or mixtures thereof. Temperature and pressure conditions are established to produce reaction with the calcium hydroxide. Propylene oxide, substantially free of methyl formate, is recovered by separation.

DESCRIPTION OF THE DRAWING

The drawing is a plot of data. The data shows the amount of calcium hydroxide which can be dissolved in aqueous glycerol solutions. The data was taken from our own work and from *Solubilities of Inorganic and Metal Organic Compounds*, 3rd ed. by A. Seidell, D. Van Nostrand Co., Inc., New York 1940, Vol. 1, p. 315.

DESCRIPTION OF THE PREFERRED EMBODIMENTS

The invention is an improvement in U.S. Pat. No. 3,477,919 incorporated herein by reference. This patent teaches the use of a calcium hydroxide slurry to remove the methyl formate contaminant from propylene oxide prepared by the epoxidation of propylene with tertiary butyl hydroperoxide. The boiling points of methyl formate and propylene oxide are very close, making separation of the two by distillation difficult.

U.S. Pat. No. 3,477,919 teaches the use of calcium hydroxide dissolved in aqueous solution to convert the methyl formate to methanol and the calcium salt of formic acid. These reaction products are easily separated from propylene oxide by conventional separation methods. For example, the separation can be effected by a simple distillation using about 40 plates. The method of this patent suffers from a single deficiency. That is, the low solubility of calcium hydroxide in water impairs the liquid phase reaction with methyl formate. To partially circumvent this deficiency, the methyl formate is treated with a calcium hydroxide slurry. Slurries are inherently more difficult to work with than a simpler all liquid phase operation.

An improvement has been discovered to the calcium hydroxide slurry method. A solubilizing agent is added to the water to improve the solubility of calcium hydroxide. This solubilizing agent is selected from the group consisting of sucrose, fructose, maltose, glycerol and mixtures thereof. It has been found experimentally that sucrose is the preferred solubilizer, followed by glycerol. Mixtures of sucrose and glycerol in water also yield good results.

The solubilizer is used in calcium hydroxide solubilizing amounts. The range of these amounts is well known in the art. They are found, for example in *Solubilities of Inorganic And Metal Organic Compounds*, 3rd ed. by A. Seidell, D. Van Nostrand Co., Inc., New York, 1940, Vol. 1, pp. 315 to 318, incorporated herein by reference. Glycerol solubility data from page 315 is plotted in the drawing.

As a general rule, about 10 wt% to about 80 wt% is the most effective working range of the solubilizer. Glycerol is typical of all the solubility agents. As seen in the drawing, below about 40 wt% glycerol, relatively large increments of glycerol yield relatively small improvements in calcium hydroxide solubility. In the range of 40 wt% to 80 wt% solubility increases approximately linearly with glycerol addition. No improvement in calcium hydroxide solubility is shown above 80 wt% glycerol. Concentrations above 60 wt% are technically feasible but are not advantageous from a processing standpoint. The concentrated solutions are viscous and scale up to industrial size quantities is not convenient. Typically the amount of solubilizer is adjusted so that the concentration of calcium hydroxide is about 4 to 6 wt% in solution.

Glycerol is most preferred. Glycerol in water is easier to use than sucrose water. At high concentration, sugar precipitates in the presence of propylene oxide, whereas the glycerol does not. The glycerol system also forms two phases making a final separation, e.g. distillation, much easier to effect. In the two phase system, water content of propylene oxide is only about 2.5 wt% whereas in the one phase sugar systems it is about 12.5 wt%. Also in the two phase system, the sodium or potassium salts of bisulfite can be added to the aqueous glycerol to remove small quantities of aldehydes, such as acetaldehyde and propenaldehyde. Treatment conditions are mild so insignificant quantities of propylene glycol are formed. The reaction with sulfite is reversible, so the aldehydes can be separated from the propylene oxide and regenerated.

It was found experimentally that glycerol-water-sugar systems worked well. However no benefit was found over the simpler sucrose-water or glycerol-water systems.

It is readily apparent from the examples that each system is subject to optimization, with the object being an improved amount of calcium hydroxide in solution. As seen in the examples, 5 to 6 wt% calcium hydroxide in solution is achievable. This is sufficient to hydrolyze methyl formate without catalyzing the reaction of propylene oxide to acetone or propylene glycol. At higher hydroxide concentrations, contact time is reduced. Temperature is also optimized in the range of 20° C. to 150° C. preferably 50° C. to 80° C. at atmospheric pressure and above to yield optimum product recovery and equipment utilization.

The ratio of crude propylene oxide to water was also found to influence methyl formate hydrolysis rate. Propylene oxide/water weight ratios of 10/1 to 5/1 were found effective. When weight ratios of 7/1 to 5/1 were used, it was found that reaction times were reduced yielding improved equipment utilization. This phenomenon is illustrated in Example VI.

The invention is distinguished in that the calcium hydroxide slurry is completely eliminated.

This invention is shown by way of example.

EXAMPLE 1

A 300 cc stainless steel autoclave was charged with 100 ml of a 1% methyl formate, 99% propylene oxide solution. The base, water and sugar were charged and the autoclave sealed. The mixture was then heated to the desired temperature for the specified time. The stirrer was maintained at 600 rpm. At the end of the reaction, the mixture was cooled to ambient temperature and any solids allowed to settle. A small sample was then taken and the products determined by GC analysis. The reaction conditions, products, etc. are reported in Table I and Table II.

Calcium oxide or calcium hydroxide solutions were prepared by stirring the appropriate quantity of base with sugar-water solutions for several hours at ambient to 40° C. No external heat was applied. The solutions were then allowed to settle and decanted from a small amount of insoluble material. In some cases, the solutions were filtered with suction and the aid of celite.

The data in Table I confirms the results of U.S. Pat. No. 3,477,919. A $CaO/Ca(OH)_2$ removes methyl formate from propylene oxide better than any of the other compounds tested.

TABLE I

Hydrolysis of Metal Formate in the Presence of Propylene Oxide[a]

| Base | grams Base | $H_2O$ grams | MeOH | MeF | Acet. | PG |
|---|---|---|---|---|---|---|
| $Na_2CO_3$ | 5.00 | 0.31 | 0.080 | 0.956 | 0.438 | 0 |
| $Na_2CO_3$ | 5.00 | 0.61 | 0.079 | 0.971 | 0.416 | 0 |
| CaO | 5.00 | 0.31 | 0.074 | 0.839 | 0.489 | 1.736 |
| CaO | 5.00 | 0.63 | 0.244 | 0.507 | 0 | 0 |
| $Na_2CO_3$ | 5.00 | 1.54 | 0.082 | 0.927 | 0.951 | 0 |
| CaO | 5.00 | 1.52 | 0.570 | 0 | 0.200 | 0 |
| $NaHCO_3$ | 5.00 | 1.00 | 0.082 | 0.935 | 0.315 | 0 |
| $Li_2CO_3$ | 5.00 | 1.00 | 0.054 | 0.710 | 1.331 | 0.008 |
| $Na_4(PO_4)_2$ | 5.00 | 1.00 | 0.024 | 0.782 | 2.702 | 0.005 |
| $Na_2B_4O_2$ | 5.00 | 1.00 | 0.044 | 0.859 | 0.533 | 0 |
| $La_2O_3$ | 5.00 | 1.00 | 0.045 | 0.562 | 0.406 | 0 |
| CaO | 5.00 | 1.00 | 0.496 | 0 | 0.050 | 0 |
| CaO | 5.00 | 2.00 | 0.485 | 0 | 0.468 | 0.021 |
| CaO | 5.00 | 5.00 | 0.481 | 0 | 0 | 0 |
| $K_2CO_3$ | 5.00 | 2.00 | 0.033 | 0.856 | 0.102 | 0 |
| $Na_2CO_3$ | 5.00 | 2.00 | 0.052 | 0.802 | 0 | 0 |
| ZnO | 5.00 | 2.00 | 0.040 | 0.835 | 0 | 0 |
| Sat. CaO soln. | 3.00 | — | 0.039 | 0.833 | 0 | 0 |
| Sat. CaO soln. | 6.00 | — | 0.043 | 0.793 | 1.067 | 0.050 |
| Sat. CaO soln. | 12.0 | — | 0.056 | 0.740 | 0 | 0.079 |
| 5% $NaHCO_3$ soln. | 5.00 | — | 0.137 | 0.564 | 0 | 0.285 |
| 5% NaOH soln. | 5.00 | — | 0.989 | 0.013 | 0.152 | 30.265 |
| CaO | 1.00 | 5.00 | 0.613 | 0.040 | 0.125 | 0 |
| CaO | 2.00 | 5.00 | 0.462 | 0.008 | 0.162 | 0.029 |
| CaO | 1.00 | 10.0 | 0.410 | 0 | 0.225 | 0.018 |

[a]60° C., 2 hours
MeOH = methanol; MeF = methyl formate; Acet. = acetone; PG = propylene glycol. Products analyzed by gas chromatograph (GC) reported in area % the equivalent of weight %. Water and propylene oxide not reported.

TABLE II

Hydrolysis of Methyl Formate in the Presence of Propylene Oxide

| Base[a] | % | Sugar | % | Wt. g | t Hr. | T °C. | MeOH | MeF | Acet. | PG |
|---|---|---|---|---|---|---|---|---|---|---|
| CaO | 5 | Sucrose | 50.0 | 50.0 | 2.0 | 60 | 0.047 | 0.859 | 0.038 | 0 |
| CaO | 5 | Sucrose | 50.0 | 10.0 | 2.0 | 60 | 0.459 | 0.045 | 0 | 0.004 |
| CaO | 5 | Sucrose | 50.0 | 20.0 | 2.0 | 60 | 0.416 | 0 | 0.821 | 0.531 |

TABLE II-continued

Hydrolysis of Methyl Formate in the Presence of Propylene Oxide

| Base[a] | % | Sugar | % | Wt. g | t Hr. | T °C. | MeOH | MeF | Acet. | PG |
|---|---|---|---|---|---|---|---|---|---|---|
| CaO | 4 | Sucrose | 20.0 | 5.0 | 2.0 | 60 | 0.115 | 0.738 | 0.241 | 0 |
| CaO | 4 | Sucrose | 20.0 | 10.0 | 2.0 | 60 | 0.437 | 0.043 | 0.183 | 0 |
| CaO | 5 | Sucrose | 30.0 | 10.0 | 2.0 | 60 | 0.457 | 0.022 | 0 | 0.481 |
| Ca(OH)$_2$ | 5 | Fructose | 30.0 | 10.0 | 2.0 | 60 | 0.204 | 0.556 | 0.272 | 0.008 |
| Ca(OH)$_2$ | 5 | Maltose | 30.0 | 10.0 | 2.0 | 60 | 0.195 | 0.531 | 0.168 | 0.712 |
| CaO | 5 | Sucrose | 30.0 | 10.0 | 2.0 | 55 | 0.427 | 0.105 | 0 | 0.156 |
| CaO | 5 | Sucrose | 30.0 | 10.0 | 1.0 | 60 | 0.393 | 0.156 | 0 | 0.098 |
| CaO | 5 | Sucrose | 30.0 | 10.0 | 1.0 | 70 | 0.425 | 0.047 | 0.564 | 0.223 |
| CaO | 5 | Sucrose | 30.0 | 15.0 | 3.0 | 50 | 0.400 | 0 | 0.073 | 0.473 |
| Ca(OH)$_2$ | 5 | Sucrose | 30.0 | 10.0 | 2.0 | 60 | 0.388 | 0.136 | 0 | 0.100 |
| Ca(OH)$_2$ | 5 | Sucrose | 30.0 | 10.0 | 4.0 | 50 | 0.401 | 0.096 | 0.068 | 0.130 |
| Ca(OH)$_2$ | 5 | Sucrose | 30.0 | 10.0 | 2.0 | 70 | 0.414 | 0.070 | 0.506 | 0.298 |
| Ca(OH)$_2$ | 5 | Sucrose | 30.0 | 15.0 | 2.0 | 60 | 0.406 | 0 | 0.118 | 0.441 |
| Ca(OH)$_2$ | Sat. | Sucrose | 30.0 | 10.0 | 2.0 | 60 | 0.379 | 0.202 | 0 | 0.156 |
| Ca(OH)$_2$ | Sat. | Sucrose | 30.0 | 10.0 | 2.0 | 70 | 0.362 | 0.270 | 0 | 0.285 |
| Ca(OH)$_2$ | Sat. | Sucrose | 30.0 | 14.5 | 2.0 | 60 | 0.624 | 0 | 0.115 | 0.165 |

[a]98% CaO - Mallinckrodt, 98% Ca(OH)$_2$ - Aldrich Area % products formed by GC, water, propylene oxide not shown. MeOH = Methanol, MeF = methyl formate, Acet. = Acetone, PG = propylene glycol

EXAMPLE II

A 300 cc stainless steel autoclave was charged with 100 ml of a 1% methyl formate, 99% propylene oxide solution. The base and glycerol-water-sugar solution was then charged and the autoclave sealed. The mixture was then heated to the desired temperature for the required time. Stirring was maintained at 600 rpm. At the end of the reaction, the mixture was cooled to ambient temperature and any solids allowed to settle. A small sample was then taken and the products determined by GC analysis. The reaction conditions, products, etc. are reported in Table III.

Calcium oxide and calcium hydroxide solutions were prepared by stirring the appropriate quantity of base with sugar-glycerol-water solutions for several hours at ambient to 40° C. No external heat was applied. The solutions were then allowed to settle and decanted from a small amount of insoluble material. In some cases, the solutions were filtered with suction and the aid of celite.

TABLE III

Hydrolysis of Methyl Formate with Ca(OH)$_2$ and Glycerol-Water-Sugar Solutions

| Base | % | Glycerol (%) | Sugar (%) | Water % | Wt. (g) | Time (Hr) | Temp °C. | MeOH | MeF | Acetone | PG |
|---|---|---|---|---|---|---|---|---|---|---|---|
| CaO | 7.1 | 71.4 | 7.1 | 14.3 | 10.0 | 2.0 | 60 | 0.469 | 0 | 0.996 | 0.96 |
| CaO | 5.9 | 44.0 | 29.4 | 20.6 | 10.0 | 2.0 | 60 | 0.496 | 0.020 | 0.062 | 0.063 |
| CaO | 7.7 | 61.5 | 15.4 | 7.7 | 15.0 | 2.0 | 60 | 0.457 | 0.007 | 0.116 | 0.288 |
| Ca(OH)$_2$ | 5.0 | 80.0 | 10.0 | 5.0 | 10.0 | 2.0 | 60 | 0.463 | 0.130 | 0.317 | 0.428 |
| Ca(OH)$_2$ | 5.0 | 80.0 | 10.0 | 5.0 | 10.0 | 2.0 | 60 | 0.395 | 0.128 | 0.456 | 0.465 |

EXAMPLE III

A 300 cc stainless steel autoclave was charged with 100 ml of a 1% methyl formate, 99% propylene oxide solution. The Ca(OH)$_2$/80% glycerol solution was then charged and the autoclave sealed. The mixture was then heated to the desired temperature for the required time. Stirring was maintained at 600 rpm. At the end of the reaction, the mixture was cooled to ambient temperature. The reaction conditions, products, etc. are reported in Table IV.

TABLE IV

Removal of Methyl Formate from Propylene Oxide

| Ca(OH)$_2$[a] (%) | Wt.[b] grams | t (Hr) | T (°C.) | MeOH | MeF | Acet. | PG |
|---|---|---|---|---|---|---|---|
| 2.5 | 10.0 | 2.0 | 60 | 0.328 | 0.345 | 0.392 | 0.346 |
| 5 | 10.0 | 2.0 | 60 | 0.364 | 0.219 | 0.218 | 0.162 |
| 5 | 10.0 | 2.0 | 60 | 0.380 | 0.171 | 0.114 | 0.187 |
| 5 | 10.0 | 4.0 | 50 | 0.346 | 0.207 | 0.753 | 0.190 |
| 5 | 10.0 | 1.0 | 70 | 0.388 | 0.143 | 0.069 | 0.120 |
| 5 | 10.0 | 2.0 | 70 | 0.398 | 0.193 | 0 | 0.153 |
| 5 | 15.0 | 2.0 | 60 | 0.459 | 0 | 0.042 | 0.605 |
| 5 | 20.0 | 2.0 | 60 | 0.380 | 0 | 0 | 0.729 |
| 1.70 | 10.0 | 2.0 | 60 | 0.227 | 0.486 | 0 | 0.202 |
| 1.70 | 10.0 | 3.0 | 60 | 0.229 | 0.504 | 0.049 | 0.198 |
| 1.70 | 10.0 | 4.0 | 60 | 0.272 | 0.411 | 0 | 0.059 |
| 1.70 | 10.0 | 1.0 | 70 | 0.206 | 0.489 | 0 | 0.294 |
| 1.70 | 20.0 | 1.0 | 60 | 0.284 | 0.256 | 0 | 0.300 |
| 1.70 | 20.0 | 2.0 | 60 | 0.388 | 0.160 | 0 | 0.906 |
| 4.35 | 10.0 | 2.0 | 60 | 0.340 | 0.207 | 0 | 0.153 |
| 4.35 | 20.0 | 2.0 | 60 | 0.390 | 0 | 0.186 | 0.610 |
| 4.57 | 10.0 | 2.0 | 60 | 0.357 | 0.185 | 0 | 0.178 |
| 4.57 | 20.0 | 2.0 | 60 | 0.460 | 0 | 0.176 | 1.073 |
| 5.52 | 10.0 | 2.0 | 60 | 0.436 | 0.012 | 0.060 | 0.347 |
| 5.52 | 20.0 | 2.0 | 60 | 0.387 | 0 | 0 | 0.844 |
| 5.84 | 15.0 | 1.0 | 50 | 0.411 | 0 | 0 | 0.123 |
| 5.84 | 15.0 | 2.0 | 50 | 0.488 | 0 | 0.248 | 0.200 |
| 5.84 | 15.0 | 3.0 | 50 | 0.433 | 0 | 0.672 | 0.414 |
| 5.84 | 15.0 | 4.0 | 50 | 0.419 | 0 | 0.068 | 0.587 |
| 5.84 | 15.0 | 1.0 | 60 | 0.412 | 0 | 0.268 | 0.362 |
| 5.84 | 15.0 | 2.0 | 60 | 0.455 | 0 | 0 | 0.577 |
| 5.84 | 15.0 | 3.0 | 60 | 0.482 | 0 | 0.897 | 1.050 |
| 5.84 | 15.0 | 1.0 | 70 | 0.427 | 0 | 0.228 | 0.581 |
| 5.84 | 15.0 | 2.0 | 70 | 0.435 | 0 | 0.170 | 0.680 |

[a]Ca(OH)$_2$ in 80% glycerol
[b]Weight of Ca(OH)$_2$ in 80% glycerol charged to the reactor

EXAMPLE IV

A. 13.5 g of 6% sodium bisulfite in 70% aqueous glycerol was added to 50.0 g impure propylene oxide in a 100 ml resin flask. Stirring speed was 300 rpm. The temperature was 20° C.±1° C. The stirrer was stopped and aliquots withdrawn and analyzed by GC.

| Time min. | Acetaldehyde wt. % | Products Propion- aldehyde wt. % | Acetone wt. % | Methanol wt. % |
|---|---|---|---|---|
| 0 | 0.020 | 0.010 | 0.301 | 0.219 |
| 3 | 0.006 | 0.004 | 0.250 | 0.155 |
| 7 | 0.005 | 0.002 | 0.258 | 0.215 |
| 15 | 0.004 | 0.004 | 0.285 | 0.151 |
| 30 | 0.018 | 0.013 | 0.332 | 0.232 |
| 60 | 0.020 | 0.014 | 0.349 | 0.288 |
| 120 | 0.021 | 0.014 | 0.340 | 0.283 |

B. The procedure was repeated except that 10.7 g of 6.00% sodium sulfite in 70% aqueous glycerol was used.

| Time min. | Acetaldehyde wt. % | Propion- aldehyde wt. % | Acetone wt. % | Methanol wt. % |
|---|---|---|---|---|
| 0 | 0.020 | 0.010 | 0.316 | 0.231 |
| 3 | 0.006 | 0.001 | 0.278 | 0.223 |
| 6 | 0.005 | 0.001 | 0.273 | 0.170 |
| 12 | 0.004 | 0.0004 | 0.240 | 0.180 |
| 20 | 0.005 | 0.002 | 0.281 | 0.213 |
| 45 | 0.005 | 0.006 | 0.317 | 0.155 |

Both acetaldehyde and propionaldehyde were removed with sodium bisulfite in aqueous glycerol. The concentration of aldehydes decreased to a minimum and then rose with time.

EXAMPLE V

A. 30.0 ml crude propylene oxide was extracted 3 times with 5.0 ml 6.00% sodium bisulfite in 70% glycerol. The results after each extraction are shown below.

|  | Acetaldehyde wt. % | Propion- aldehyde wt. % | Acetone wt. % | Methanol wt. % |
|---|---|---|---|---|
| Starting Material | 0.020 | 0.010 | 0.301 | 0.219 |
| First extraction | 0.007 | 0.007 | 0.280 | 0.200 |
| Second extraction | 0.006 | 0.006 | 0.278 | 0.135 |
| Third extraction | 0.005 | 0.004 | 0.205 | 0.089 |

B. The procedure, was repeated except that 14.3 g 6% sodium metabisulfite in 70% glycerol (temp.=13° C.±1° C.) was used.

| Time min. | Acetaldehyde wt. % | Products Propion- aldehyde wt. % | Acetone wt. % | Methanol wt. % |
|---|---|---|---|---|
| 0 | 0.020 | 0.010 | 0.301 | 0.219 |
| 3 | 0.007 | 0.007 | 0.289 | 0.204 |
| 6 | 0.005 | 0.005 | 0.253 | 0.145 |
| 12 | 0.006 | 0.004 | 0.218 | 0.153 |
| 28 | 0.005 | 0.003 | 0.144 | 0.150 |
| 60 | 0.004 | 0.0006 | 0.093 | 0.161 |
| 120 | 0.005 | 0.005 | 0.111 | 0.199 |

EXAMPLE VI

A. A 100 ml resin flask equipped with an overhead stirrer, thermometer, and water cooled condenser was charged with 50.0 g methyl formate in propylene oxide. The mixture was stirred at 300 rpm and the temperature maintained by means of a resistance heater suspended in a small water bath. Calcium hydroxide (0.42 g) was charged along with 10.0 g water. Aliquots were withdrawn at the time indicated and analyzed by GC. The results are reported here.

| Time (min) | Temp. (°C.) | MeOH Wt. % | MeF Wt. % | H$_2$O Wt. % | PO Wt. % |
|---|---|---|---|---|---|
| 0 | 30.2 | trace | 0.879 | — | — |
| 2 | 30.5 | 0.191 | 0.516 | — | — |
| 5 | 31.0 | 0.361 | 0.053 | — | — |
| 10 | 30.0 | 0.353 | ~0 | — | — |
| 16 | 29.8 | 0.432 | ~0 | — | — |
| 30 | 29.8 | 0.474 | ~0 | 14.47 | 85.18 |
| (lower layer) |  | 0.619 | ~0 | 79.76 | 19.35 |

B. The procedure was the same as A, except that 5.0 g water was charged.

| Time (min) | Temp. (°C.) | MeOH Wt. % | MeF Wt. % | H$_2$O Wt. % | PO Wt. % |
|---|---|---|---|---|---|
| 0 | 30.0 | trace | 0.881 | — | — |
| 2 | 29.9 | 0.068 | 0.782 | — | — |
| 5 | 30.5 | 0.112 | 0.702 | — | — |
| 10 | 29.9 | 0.115 | 0.681 | — | — |
| 30 | 30.2 | 0.214 | 0.588 | — | — |
| 60 | 30.1 | 0.248 | 0.499 | 12.40 | 86.95 |

C. The procedure was the same as A, except that 7.0 g water was used.

| Time (min) | Temp. (°C.) | MeOH Wt. % | MeF Wt. % | H$_2$O Wt. % | PO Wt. % |
|---|---|---|---|---|---|
| 0 | 29.2 | trace | 0.877 | — | — |
| 2 | 29.8 | 0.080 | 0.747 | — | — |
| 6 | 30.8 | 0.316 | 0.368 | — | — |
| 12 | 29.8 | 0.340 | 0.294 | — | — |
| 18 | 30.0 | 0.437 | 0.226 | — | — |
| 30 | 30.0 | 0.445 | 0.143 | — | — |
| 60 | 30.1 | 0.440 | 0.025 | 14.76 | 84.77 |

D. The procedure was the same as A except that 8.0 g water was charged.

| Time (min) | Temp. (°C.) | MeOH Wt. % | MeF Wt. % | H$_2$O Wt. % | PO Wt. % |
|---|---|---|---|---|---|
| 0 | 30.0 | trace | 0.877 | — | — |
| 2 | 29.5 | 0.193 | 0.526 | — | — |
| 4 | 30.0 | 0.383 | 0.196 | — | — |
| 9 | 29.0 | 0.388 | 0.091 | — | — |
| 16 | 29.1 | 0.463 | 0.031 | — | — |
| 30 | 29.6 | 0.522 | 0.003 | 14.71 | 84.84 |

E. The procedure was the same as A, except that 6.0 g water was charged.

| Time (min) | Temp. (°C.) | MeOH Wt. % | MeF Wt. % | H$_2$O Wt. % | PO Wt. % |
|---|---|---|---|---|---|
| 0 | 28.2 | trace | 0.870 | — | — |
| 2 | 29.5 | 0.051 | 0.811 | — | — |
| 6 | 30.3 | 0.098 | 0.701 | — | — |
| 15 | 29.5 | 0.123 | 0.678 | — | — |

-continued

| Time (min) | Temp. (°C.) | MeOH Wt. % | MeF Wt. % | H$_2$O Wt. % | PO Wt. % |
|---|---|---|---|---|---|
| 30 | 29.7 | 0.159 | 0.612 | — | — |
| 60 | 30.0 | 0.226 | 0.535 | 12.62 | 86.68 |

F. The procedure was the same as A, except that 6.5 g water was used.

| Time (min) | Temp. (°C.) | MeOH Wt. % | MeF Wt. % | H$_2$O Wt. % | PO Wt. % |
|---|---|---|---|---|---|
| 0 | 28.0 | trace | 0.877 | — | — |
| 2 | 29.4 | 0.071 | 0.788 | — | — |
| 5 | 30.6 | 0.181 | 0.573 | — | — |
| 12 | 30.1 | 0.240 | 0.478 | — | — |
| 18 | 29.8 | 0.243 | 0.463 | — | — |
| 30 | 29.9 | 0.254 | 0.416 | — | — |
| 60 | 30.0 | 0.378 | 0.296 | 13.37 | 85.96 |

G. The procedure was the same as A, except that 8.0 g water was used and the stirring speed was 600 rpm.

| Time (min) | Temp. (°C.) | MeOH Wt. % | MeF Wt. % | H$_2$O Wt. % | PO Wt. % |
|---|---|---|---|---|---|
| 0 | 28.2 | trace | 0.879 | — | — |
| 2 | 29.1 | 0.191 | 0.670 | — | — |
| 6 | 30.3 | 0.495 | 0.119 | — | — |
| 12 | 30.0 | 0.471 | 0.045 | — | — |
| 30 | 30.0 | 0.569 | ~0 | 13.30 | 86.25 |

H. The procedure was the same as that described in A, except that 8.0 g water was used and the stirring rate was 200 rpm.

| Time (min) | Temp. (°C.) | MeOH Wt. % | MeF Wt. % | H$_2$O Wt. % | PO Wt. % |
|---|---|---|---|---|---|
| 0 | 27.8 | trace | 0.870 | — | — |
| 2 | 28.6 | 0.149 | 0.659 | — | — |
| 6 | 30.3 | 0.481 | 0.152 | — | — |
| 10 | 29.7 | 0.538 | 0.096 | — | — |
| 15 | 30.0 | 0.478 | 0.062 | — | — |
| 30 | 29.8 | 0.477 | 0.011 | 14.22 | 85.32 |

I. The procedure was the same as A, except that 8.0 g water and 0.296 g calcium hydroxide were used.

| Time (min) | Temp. (°C.) | MeOH Wt. % | MeF Wt. % | H$_2$O Wt. % | PO Wt. % |
|---|---|---|---|---|---|
| 0 | 28.0 | trace | 0.867 | — | — |
| 2 | 29.2 | 0.143 | 0.616 | — | — |
| 5 | 30.9 | 0.387 | 0.179 | — | — |
| 10 | 30.2 | 0.422 | trace | — | — |
| 15 | 30.0 | 0.649 | trace | — | — |
| 30 | 29.8 | 0.587 | ~0 | 14.81 | 84.68 |

J. The procedure was the same as A, except that 8.0 g water was used and the temperature was maintained at 21° C.±1° C.

| Time (min) | Temp. (°C.) | MeOH Wt. % | MeF Wt. % | H$_2$O Wt. % | PO Wt. % |
|---|---|---|---|---|---|
| 0 | 19.5 | 0.007 | 0.850 | — | — |
| 2 | 20.0 | 0.087 | 0.721 | — | — |
| 5 | 21.0 | 0.223 | 0.430 | — | — |
| 10 | 21.2 | 0.402 | 0.090 | — | — |
| 16 | 21.0 | 0.488 | 0.041 | — | — |
| 22 | 21.1 | 0.458 | 0.024 | — | — |
| 45 | 21.0 | 0.049 | ~0 | 12.47 | 87.12 |

K. The procedure was the same as that described in A, except that 8.0 g water was used and the temperature was maintained at 1° C./±1° C.

| Time (min) | Temp. (°C.) | MeOH Wt. % | MeF Wt. % | H$_2$O Wt. % | PO Wt. % |
|---|---|---|---|---|---|
| 0 | 1.0 | 0.008 | 0.848 | — | — |
| 2 | 1.0 | 0.040 | 0.807 | — | — |
| 5 | 0.9 | 0.069 | 0.745 | — | — |
| 15 | 1.2 | 0.211 | 0.461 | — | — |
| 21 | 0.4 | 0.312 | 0.313 | — | — |
| 30 | 0.1 | 0.365 | 0.158 | — | — |
| 45 | 1.7 | 0.389 | 0.064 | — | — |
| 62 | 1.2 | 0.390 | 0.033 | 11.07 | 88.50 |

L. The procedure was the same as A, except that 8.0 g water was used and the temperature was maintained at 10° C.±1° C.

| Time (min) | Temp. (°C.) | MeOH Wt. % | MeF Wt. % | H$_2$O Wt. % | PO Wt. % |
|---|---|---|---|---|---|
| 0 | 8.5 | trace | 0.855 | — | — |
| 2 | 8.9 | 0.052 | 0.772 | — | — |
| 5 | 9.2 | 0.145 | 0.609 | — | — |
| 10 | 10.0 | 0.234 | 0.366 | — | — |
| 15 | 10.0 | 0.344 | 0.170 | — | — |
| 22 | 9.7 | 0.449 | 0.055 | — | — |
| 33 | 10.0 | 0.434 | ~0.01 | — | — |
| 45 | 10.0 | 0.458 | ~0 | 11.89 | 87.71 |

Many modifications may be made to the method of this invention without departing from the spirit and scope of the invention which is defined only in the appended claims. For example, one skilled in the art could adjust the temperature, pressure and modes of contacting, either batch, semi-batch or continuous to provide propylene oxide free of the methyl formate contaminant.

What is claimed is:

1. A method for removing methyl formate from propylene oxide which comprises:
    contacting propylene oxide containing methyl formate with aqueous calcium hydroxide in an amount at least stoichiometrically equivalent to the methyl formate and a solubilizing amount of a solubilizing compound selected from the group consisting of sucrose, fructose, maltose, glycerol and mixtures thereof,
    establishing temperature and pressure conditions which produce a reaction between methyl formate and the calcium hydroxide and
    separating and recovering propylene oxide substantially free of methyl formate.

2. The method of claim 1 wherein the calcium hydroxide is in an amount about 1.25 times the stoichiometric equivalent of methyl formate present.

3. The method of claim 1 wherein the solubilizing compound is selected from the group consisting of sucrose, glycerol and mixtures thereof.

4. The method of claim 1 wherein the solubilizing compound is sucrose.

5. The method of claim 1 wherein the solubilizing compound is glycerol.

6. The method of claim 1 wherein the solubilizing compound is present in an amount of 10 to 80 wt%.

7. The method of claim 1 wherein the solubilizing compound is present in an amount of 40 to 60 wt%.

8. The method of claim 1 wherein the concentration of calcium hydroxide is about 4 to 6 wt%.

9. The method of claim 1 wherein the weight ratio of propylene oxide to water is about 10/1 to 5/1.

10. The method of claim 1 wherein the weight ratio of propylene oxide to water is about 7/1 to 5/1.

11. A method for purifying crude propylene oxide contaminated with methyl formate and aldehydes which comprises:

contacting crude propylene oxide with aqueous calcium hydroxide in an amount at least stoichiometrically equivalent to the methyl formate and a solubilizing amount of glycerol and an aldehyde scavenger selected from the group consisting of the sodium and potassium salts of bisulfite in an amount at least stoichiometrically equivalent to the aldehydes, establishing temperature and pressure conditions which produce a reaction between methyl formate and the calcium hydroxide and separating and recovering propylene oxide substantially free of methyl formate and aldehydes.

12. The method of claim 11 wherein the calcium hydroxide is in an amount about 1.25 times the stoichiometric equivalent of methyl formate present.

13. The method of claim 11 wherein the glycerol is present in an amount of 10 to 80 wt%.

14. The method of claim 11 wherein the glycerol is present in an amount of 40 to 60 wt%.

15. The method of claim 11 wherein the concentration of calcium hydroxide is about 4 to 6 wt%.

16. The method of claim 11 wherein the aldehyde scavenger is present in an amount about 1.25 times the stoichiometric equivalent of the aldehydes present.

17. The method of claim 11 wherein the weight ratio of propylene oxide to water is about 10/1 to 5/1.

18. The method of claim 11 wherein the weight ratio of propylene oxide to water is about 7/1 to 5/1.

* * * * *